(12) United States Patent
Kanios

(10) Patent No.: US 9,668,981 B2
(45) Date of Patent: *Jun. 6, 2017

(54) DEVICE FOR TRANSDERMAL ADMINISTRATION OF DRUGS INCLUDING ACRYLIC BASED POLYMERS

(71) Applicant: Noven Pharmaceuticals, Inc., Miami, FL (US)

(72) Inventor: David Kanios, Palmetto Bay, FL (US)

(73) Assignee: NOVEN PHARMACEUTICALS, INC., Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/091,939

(22) Filed: Apr. 6, 2016

(65) Prior Publication Data

US 2017/0065535 A1 Mar. 9, 2017

Related U.S. Application Data

(63) Continuation of application No. 14/713,252, filed on May 15, 2015, now Pat. No. 9,333,263, which is a (Continued)

(51) Int. Cl.
A61K 9/70 (2006.01)
A61K 9/00 (2006.01)
A61K 31/4458 (2006.01)

(52) U.S. Cl.
CPC .......... *A61K 9/7023* (2013.01); *A61K 9/0014* (2013.01); *A61K 9/7061* (2013.01); *A61K 9/7069* (2013.01); *A61K 31/4458* (2013.01)

(58) Field of Classification Search
CPC .. A61K 9/7023; A61K 9/0014; A61K 9/7069; A61K 9/7061; A61K 31/4458
See application file for complete search history.

(56) References Cited

U.S. PATENT DOCUMENTS

| 4,390,520 A | 6/1983 | Nagai et al. |
| 4,559,222 A | 12/1985 | Enscore et al. |

(Continued)

FOREIGN PATENT DOCUMENTS

| EP | 0 827 741 | 3/1998 |
| EP | 0 887 075 | 12/1998 |

(Continued)

OTHER PUBLICATIONS

Satas, "Acrylic Adhesives," *Handbook of Pressure-Sensitive Adhesive Technology*, $2^{nd}$ ed., D. Satas, ed., pp. 396-456, Van Nostrand Reinhold, New York (1989).

(Continued)

*Primary Examiner* — Trevor Love
(74) *Attorney, Agent, or Firm* — Foley & Lardner LLP

(57) ABSTRACT

A transdermal delivery system is provided where the drug delivery rates, onset and profiles of at least one active agent are controlled by selectively manipulating the monomeric make up of an acrylic-based polymer in the transdermal drug delivery system. The drug carrier composition may be comprised of (a) one or more acrylic-based polymers having one or more different monomers selected from the group consisting of hard and soft monomers; (b) one or more silicone-based polymers; and (c) one or more active agents where the device provides a desired solubility for the active agent and controls drug delivery rates, onset and profiles of at least one active agent.

18 Claims, 4 Drawing Sheets

Related U.S. Application Data continuation of application No. 14/133,900, filed on Dec. 19, 2013, now Pat. No. 9,034,370, which is a continuation of application No. 13/229,007, filed on Sep. 9, 2011, now Pat. No. 8,632,802, which is a continuation of application No. 11/245,097, filed on Oct. 7, 2005, now abandoned.

(60) Provisional application No. 60/616,860, filed on Oct. 8, 2004.

(56) References Cited

U.S. PATENT DOCUMENTS

| | | | |
|---|---|---|---|
| 4,584,355 | A | 4/1986 | Blizzard et al. |
| 4,585,836 | A | 4/1986 | Homan et al. |
| 4,591,622 | A | 5/1986 | Blizzard et al. |
| 4,655,767 | A | 4/1987 | Woodard et al. |
| 4,938,759 | A | 7/1990 | Enscore et al. |
| 4,994,267 | A | 2/1991 | Sablotsky et al. |
| 4,994,278 | A | 2/1991 | Sablotsky et al. |
| 5,032,207 | A | 7/1991 | Sablotsky et al. |
| 5,405,486 | A | 4/1995 | Sablotsky et al. |
| 5,446,070 | A | 8/1995 | Mantelle |
| 5,474,783 | A | 12/1995 | Miranda |
| 5,474,787 | A | 12/1995 | Grey et al. |
| 5,505,956 | A | 4/1996 | Kim et al. |
| 5,656,285 | A | 8/1997 | Sablotsky et al. |
| 5,656,286 | A | 8/1997 | Miranda et al. |
| 5,665,377 | A | 9/1997 | Gonella |
| 5,693,335 | A | 12/1997 | Xia et al. |
| 5,725,876 | A | 3/1998 | Mantelle et al. |
| 5,730,999 | A | 3/1998 | Lehmann et al. |
| 5,762,952 | A | 6/1998 | Barnhart et al. |
| 5,904,931 | A | 5/1999 | Lipp et al. |
| 5,958,446 | A | 9/1999 | Miranda et al. |
| 6,024,976 | A | 2/2000 | Miranda et al. |
| 6,162,456 | A | 12/2000 | Dunbar et al. |
| 6,221,383 | B1 | 4/2001 | Miranda et al. |
| 6,235,306 | B1 | 5/2001 | Miranda et al. |
| 6,316,022 | B1 | 11/2001 | Mantelle et al. |
| 6,562,363 | B1 | 5/2003 | Mantelle et al. |
| 6,638,528 | B1 | 10/2003 | Kanios |
| 7,993,671 | B2 | 8/2011 | Mantelle et al. |
| 8,586,080 | B1 | 11/2013 | Hartwig et al. |
| 8,632,802 | B2 | 1/2014 | Kanios |
| 8,916,191 | B2 | 12/2014 | Kanios |
| 9,034,370 | B2 | 5/2015 | Kanios |
| 9,333,263 | B2 | 5/2016 | Kanios |
| 2003/0228354 | A1 | 12/2003 | Muraoka et al. |
| 2005/0169977 | A1 | 8/2005 | Kanios et al. |
| 2006/0078601 | A1 | 4/2006 | Kanios et al. |
| 2006/0078604 | A1 | 4/2006 | Kanios et al. |
| 2006/0233870 | A1 | 10/2006 | Houze et al. |
| 2006/0240087 | A1 | 10/2006 | Houze et al. |

FOREIGN PATENT DOCUMENTS

| | | |
|---|---|---|
| JP | 04-117323 A | 4/1992 |
| JP | 09-301854 A | 11/1997 |
| WO | WO 95/31193 A1 | 11/1995 |
| WO | WO 00/33812 | 6/2000 |
| WO | WO-00/51575 | 9/2000 |
| WO | WO-00/64418 | 11/2000 |

OTHER PUBLICATIONS

Kine et al., "Acrylic and Methacrylic Ester Polymers," *Polymer Science and Engineering*, vol. 1, 2$^{nd}$ ed., John Wiley and Sone, pp. 234-299, 1984.

Merck & Co., *Merck Index*, 12$^{th}$ ed., pp. THER1-THER28, Rahway, NJ, 1981.

Merck & Co., Merck Index, 11$^{th}$ ed., pp. THER5-THER29, Rahway, NJ, 1980.

Vaughan et al., "Using solubility parameters in cosmetics formulation," J. Soc. Cosmet. Chem., vol. 36, pp. 319-333, Sep./Oct. 1985.

Sobieski et al., "Silicone Pressure Sensitive Adhesieves," Handbook of Pressure-Sensitive Adhesive Technology, 2$^{nd}$ ed., pp. 508-517, 1989.

Office Action issued Jun. 18, 2009, by the Examiner in U.S. Appl. No. 11/256,190 (US 2006-0240087).

Office Action issued Feb. 4, 2009, by the Examiner in U.S. Appl. No. 11/256,190 (US 2006-0240087).

Office Action issued Aug. 20, 2008, by the Examiner in U.S. Appl. No. 11/256,190 (US 2006-0240087).

Office Action issued Nov. 30, 2007, by the Examiner in U.S. Appl. No. 11/256,190 (US 2006-0240087).

Office Action issued Mar. 5, 2007, by the Examiner in U.S. Appl. No. 11/256,190 (US 2006-0240087).

Office Action issued Sep. 8, 2009, by the Examiner in U.S. Appl. No. 11/256,189 (US 2006-0233870).

Office Action issued Mar. 13, 2009, by the Examiner in U.S. Appl. No. 11/256,189 (US 2006-0233870).

Office Action issued Aug. 26, 2008, by the Examiner in U.S. Appl. No. 11/256,189 (US 2006-0233870).

Office Action issued Mar. 5, 2008, by the Examiner in U.S. Appl. No. 11/256,189 (US 2006-0233870).

Office Action issued Jun. 11, 2007, by the Examiner in U.S. Appl. No. 11/256,189 (US 2006-0233870).

Office Action issued Feb. 20, 2007, by the Examiner in U.S. Appl. No. 11/256,189 (US 2006-0233870).

Office Action issued on Feb. 4, 2011 by the Examiner in U.S. Appl. No. 11/245,097 (US 2006/0078602).

Office Action issued on Aug. 20, 2010 by the Examiner in U.S. Appl. No. 11/245,097 (US 2006/0078602).

Office Action issued on Dec. 16, 2009 by the Examiner in U.S. Appl. No. 11/245,097 (US 2006/0078602).

Office Action issued on Jul. 21, 2009 by the Examiner in U.S. Appl. No. 11/245,097 (US 2006/0078602).

Office Action issued on Jan. 7, 2009 by the Examiner in U.S. Appl. No. 11/245,097 (US 2006/0078602).

Office Action issued on Jul. 29, 2008 by the Examiner in U.S. Appl. No. 11/245,097 (US 2006/0078602).

Office Action issued on Aug. 22, 2012 by the Examiner in U.S. Appl. No. 13/229,007 (U.S. Pat. No. 8,632,802).

Office Action issued on Feb. 17, 2013 by the Examiner in U.S. Appl. No. 13/229,007 (U.S. Pat. No. 8,632,802).

Office Action issued on Aug. 16, 2013 by the Examiner in U.S. Appl. No. 13/229,007 (U.S. Pat. No. 8,632,802).

Notice of Allowance issued on Dec. 5, 2013 by the Examiner in U.S. Appl. No. 13/229,007 (U.S. Pat. No. 8,632,802).

Notice of Allowance issued on Aug. 13, 2014 in U.S. Appl. No. 14/245,398 (U.S. Pat. No. 8,916,191).

Kardavilli et al., "Polymers in Transdermal Drug Delivery Systems," Pharmaceutical Technology, pp. 62-80, May 2002.

Evoniks Industries, "Eudragit NE 40 D," http://eudragit.evonik.com/product/eudragit/en/products-services/eudragit-products/sustain, accessed Aug. 12, 2013.

Minghetti et al., "Dermal Patches for the Controlled Release of Miconazole: Influence of the Drug Concentration on the Technological Characteristics," Drug Development and Industrial Pharmacy, vol. 25, No. 5, pp. 679-684, 1999.

Notice of Allowance issued on Feb. 10, 2015 in U.S. Appl. No. 14/133,900 (U.S. Pat. No. 9,034,370).

Notice of Allowance issued on Jan. 2, 2016 in U.S. Appl. No. 14/713,252 (U.S. Pat. No. 9,333,263).

DEVICE FOR TRANSDERMAL ADMINISTRATION OF DRUGS INCLUDING ACRYLIC BASED POLYMERS

This application claims the benefit of provisional application 60/616,860 filed Oct. 8, 2004, which is hereby incorporated by reference in its entirety.

FIELD OF THE INVENTION

This invention relates generally to transdermal drug delivery systems, and more particularly to pharmaceutically acceptable adhesive matrix compositions. The invention additionally relates to transdermal drug delivery systems where the drug permeation, delivery rates and profiles can be selectively modulated within the transdermal drug delivery system.

BACKGROUND OF THE INVENTION

The use of transdermal drug delivery systems to topically administer an active agent is well known. These systems incorporate the active agent into a carrier composition, such as a polymeric and/or pressure-sensitive adhesive composition, from which the active agent is delivered through the skin or mucosa of the user.

Active-ingredient-containing transdermal drug delivery systems ("patches") are essentially divided into two major technical systems: reservoir systems and matrix systems. The present invention relates to matrix systems where the active ingredient(s) are embedded in a semi-solid matrix made up of a single polymer or a blend of polymers.

Both types of devices employ a backing layer that forms the protective outer surface of the finished transdermal system and which is exposed to the environment during use. A release liner or protective layer that forms the inner surface covers the polymeric adhesive which is employed for affixing the system to the skin or mucosa of a user. The release liner or protective layer is removed prior to application, exposing the adhesive, typically a pressure-sensitive adhesive.

In the "classic" reservoir-type device, the active agent is typically dissolved or dispersed in a carrier to yield a non-finite carrier form, such as, for example, a fluid or gel. In the reservoir-type device, the active agent is generally kept separate from the adhesive. The device has a pocket or "reservoir" which physically serves to hold the active agent and carrier, and which is formed in or by a backing layer. A peripheral adhesive layer is then used to affix the device to the user.

The reservoir-type devices have a number of disadvantages including a non-uniform drug release profile where a high dose of drug is initially released upon application to the user, often described as a "burst effect." This burst or high initial release of drug then drops off after a period of time to a rate that necessary to achieve a therapeutically effective amount. Drug delivery according to this profile is generally described as first order release.

While classic reservoir-type devices are still in use today, the term reservoir is being used interchangeably herein with matrix-type devices which still rely upon a separate adhesive means used to affix the device to the user.

In a matrix-type device, the active agent is dissolved or dispersed in a carrier that typically is in a finite carrier form. The carrier form can be self-adhesive or non-adhesive. Non-adhesive matrix-type devices, that is, those which still rely on a separate adhesive means to affix the device to the user, employ a drug permeable adhesive layer (often referred to as an "in-line adhesive" since the drug must pass through this layer) applied over the drug matrix carrier layer. To better control the release rate of the drug, the non-adhesive matrix-type devices often employ one or more additional drug permeable layers such as, for example, rate controlling membranes. The non-adhesive matrix-type devices often contain excipients, such as drug delivery enhancers, to help control the release rate. These devices are often referred to as multilayer or multilaminate.

In a "monolithic" or "monolayer" matrix-type device, the active agent is typically solubilized or homogenously blended in an adhesive carrier composition, typically a pressure-sensitive adhesive or bioadhesive, which functions as both the drug carrier and the means of affixing the system to the skin or mucosa. Such devices, commonly referred to as drug-in-adhesive devices, are described, for example, in U.S. Pat. Nos. 4,994,267; 5,446,070; 5,474,783 and 5,656,286, all of which are assigned to Noven Pharmaceuticals, Inc., Miami, Fla. and herein incorporated by reference.

While matrix-type devices, especially drug-in-adhesive devices, achieve more uniform and controlled drug deliver rates over longer periods of time, most transdermal systems remain subject to a higher initial drug release than is required to achieve therapeutic efficacy. For many drugs and/or therapeutic situations, it would be advantageous to eliminate or suppress this higher initial release and achieve a "steady state" (zero order) release profile which uniformly delivers a therapeutically effective amount of drug over the extended duration of device's desired use, preferably up to 7 days or more.

The high initial blood level concentration of certain drugs may cause adverse or undesired effects, or create toxicity concerns, thereby limiting the use of transdermal administration. In other instances, the higher initial blood level concentration may reduce the amount of drug required for treatment to the point of risking under dosing, or the higher initial blood level concentration may make it impractical to increase the duration of the device's application while retaining therapeutic effectiveness. Reducing the frequency of replacing the transdermal drug delivery system would increase user compliance, reduce any lag or drop off in efficacious blood levels, and reduce the amount of drug required for treatment (also provided by reducing the higher initial blood level associated with the higher release rate).

Drug concentration in transdermal delivery systems can vary widely depending on the drug and polymers used. Low drug concentrations in the adhesive can result in difficulties in achieving art acceptable delivery rate of the medicament, preferably one approximating zero order kinetics. High drug concentrations, on the other hand, frequently affect the adhesion properties of the adhesives, and tend to promote unwanted crystallization.

Simple diffusion models for permeation of drugs through the skin suggest that permeation rates are concentration dependent, that is, dependent on both the amount and the degree of drug within the pressure-sensitive adhesive composition. Some adhesives, such as, for example, polyacrylate adhesives have a high affinity for many drugs and thus tend to solubilize higher concentrations of drug than do, for example, rubber adhesives. However, the use of polyacrylates alone as the adhesive is not without its drawbacks as polyacrylate adhesives, for example, may tend to cause skin irritation, especially when the transdermal device is used for extended periods of time.

Therefore, despite the existence of many different types of transdermal delivery systems in the art, there remains a continuing need for improving the selective modulation of drug permeation, delivery rates and drug profiles in transdermal delivery systems.

SUMMARY OF THE INVENTION

Based upon the foregoing, it is an object of the present invention to overcome the limitations of the prior transdermal systems, and to provide a transdermal drug delivery system which allows selective modulation of drug permeation and delivery rates and profiles.

Another object is to provide a transdermal system, which is simple and inexpensive to manufacture. The present invention provides a transdermal drug delivery system for the topical application of one or more active agents contained in one or more polymeric and/or adhesive carrier layers which is manufactured to optimize drug loading while providing desirable adhesion to skin or mucosa as well as providing modulation of the drug delivery and profile.

The invention is also directed to compositions and methods of controlling drug delivery rates, onset and profiles of at least one active agent in a transdermal delivery system by selectively manipulating the monomeric make up of an acrylic-based polymer in the transdermal drug delivery system. The drug carrier composition may be comprised of (a) one or more acrylic-based polymers having one or more different monomers selected from the group consisting of hard and soft monomers; (b) one or more silicone-based polymers having one or more silanol contents (capping) and/or resin to polymer ratios and or a rubber; and (c) one or more active agents where the device provides a desired solubility for the active agent and controls drug delivery rates, onset and profiles of at least one active agent. Further manipulation of drug delivery, onset and profiles can be achieved by varying the concentrations of the drug in the drug-loaded carrier.

Further embodiments of the invention include those described in the detailed description.

DETAILED DESCRIPTION OF THE PREFERRED EMBODIMENTS

Figure 1:
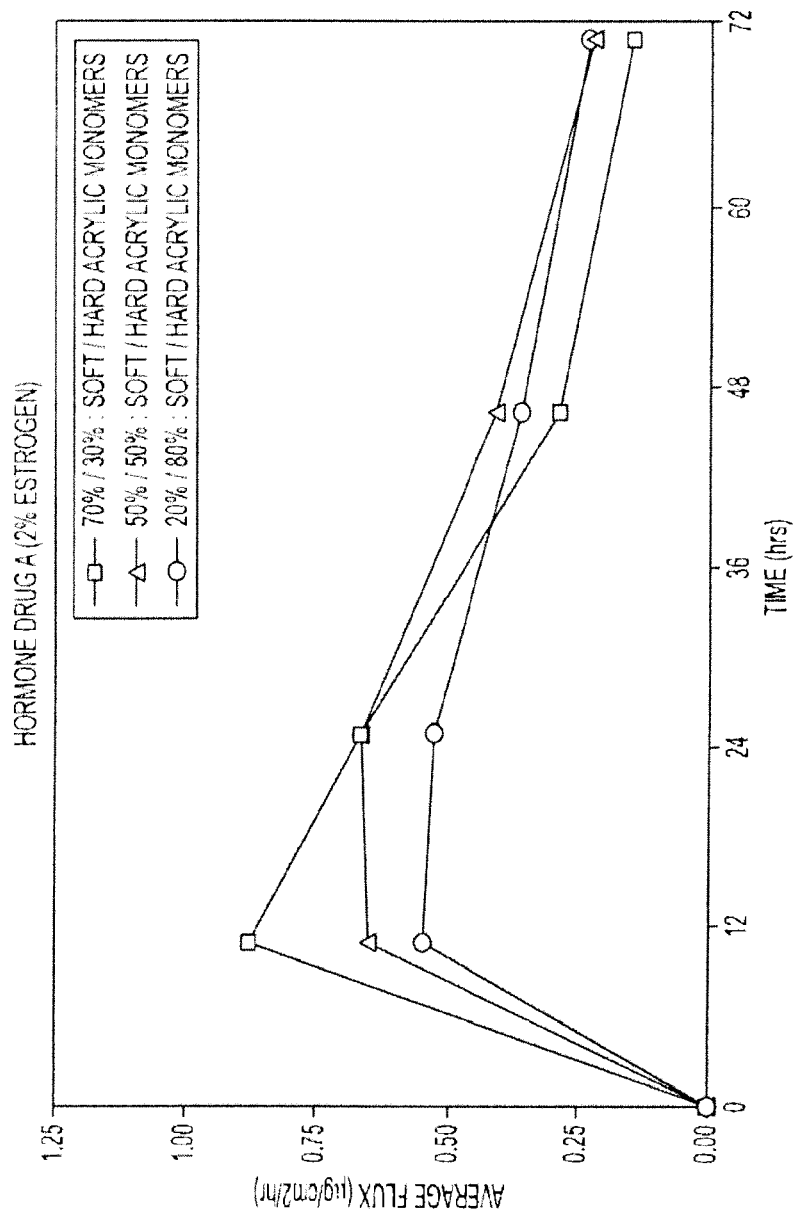
FIG. 1 is a graphic representation of the effects on drug delivery, onset and profile of 17β-estradiol with different proportions of hard and soft acrylic-based monomers in the pressure sensitive adhesives.

The foregoing and other objects are achieved by this invention which provides a transdermal drug delivery system to provide an adhesive matrix composition which effectively delivers drugs to a user over an extended period of time.

Unless defined otherwise, all technical and scientific terms used herein have the same meaning as commonly understood by one of ordinary skill in the art to which the invention pertains.

The invention relates to a pressure-sensitive adhesive composition comprising a single polymer or a blend of at least two polymers together with a drug. The blend of at least two polymers is preferred and is herein referred to as a multiple polymer adhesive system. The term "blend" is used herein to mean that there is no, or substantially no, chemical reaction or cross-linking (other than simple H-bonding) between the different polymers in the multiple polymer adhesive system.

As used herein, the term "pressure-sensitive adhesive" refers to a viscoelastic material which adheres almost instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term pressure-sensitive adhesive also includes mixtures of different polymers and mixtures of polymers, such as polyisobutylenes (PIB) of different molecular weights, the resultant mixtures being a pressure-sensitive adhesive. In the last case, the polymers of lower molecular weight in the mixture are not considered to be "tackifiers," the term "tackifier" being reserved for additives which differ other than in molecular weight from the polymers to which they are added.

The term "topical" or "topically" is used herein in its conventional meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces.

The term "transdermal" as used herein means passage into and/or through skin or mucosa for localized or systemic delivery of an active agent.

The term "solubilized" is intended to mean that in the carrier composition there is an intimate dispersion or dissolution of the active agent at the crystalline, molecular or ionic level. As such, the solubilized active agent is considered herein to be in "non-crystallized" form when in the compositions of the present invention.

The phrase "pharmaceutically acceptable flexible, finite" is intended to mean a solid form capable of conforming to a surface to which it is applied, and which is capable of maintaining the contact in such solid form so as to facilitate topical application without adverse physiological response, and without being appreciably decomposed by aqueous contact during use by a subject.

The term "user" or "subject" is intended to include all warm-blooded mammals, preferably humans.

The phrase "substantially zero-order" as used herein means transdermal delivery of an active agent at a release rate which is approximately constant once steady state is attained, typically within 12 to 24 hours after topical application. While variability in blood levels of active agent are contemplated within the scope of this meaning once steady state release is attained, the depletion rate of active agent over the duration of use should typically not exceed about 20% to about 25%.

The term "active agent" (and its equivalents "agent," "drug," "medicament" and "pharmaceutical") is intended to have the broadest meaning and includes at least one of any therapeutic, prophylactic, pharmacological or physiological active substance, cosmetic and personal care preparations, and mixtures thereof, which is delivered to a mammal to produce a desired, usually beneficial, effect. More specifically, any active agent that is capable of producing a pharmacological response, localized or systemic, irrespective of whether therapeutic, diagnostic, cosmetic or prophylactic in nature, is within the contemplation of the invention. Also within the invention are such bioactive agents as pesticides, insect repellents, sun screens, cosmetic agents, etc. It should be noted that the drugs and/or bioactive agents may be used singularly or as a mixture of two or more such agents, and in amounts sufficient to prevent, cure, diagnose or treat a disease or other condition, as the case may be. In the case of drugs, the drug can be in its free base or acid form, or in the form of salts, esters, amides, prodrugs, enantiomers or mixtures thereof, or any other pharmacologically acceptable derivatives, or as components of molecular complexes The drug is used in a "pharmacologically effective amount." This term means that the concentration of the drug is such that in the composition it results in a therapeutic level of drug delivered over the term that the transdermal dosage form is to be used, preferably with zero order kinetics. Such delivery is dependent on a great number of variables including the drug, the time period for which the individual dosage unit is to be used, the flux rate of the drug from the system and a number of other variables. The amount of drug needed can be experimentally determined based on the flux rate of the drug through the system and through the skin when used with and without enhancers. Having determined the flux rate needed, the transdermal delivery system is designed so that the release rate over the period of time of therapeutic use will be at least equal to the flux rate. Of course, the surface area of the transdermal delivery system also affects the delivery of the drug from the system.

Drugs in general can be used in this invention. These drugs include those categories and species of drugs set forth on page then-5 to then-29 of the *Merck Index*, 11th Edition Merck & Co. Rahway, N.J. (1989).

Exemplary of drugs that can be administered by the novel dermal drug delivery system include, but are not limited to:

1. Central nervous system stimulants and agents such as Dextroamphetamine, Amphetamine, Methamphetamine, D-Amphetamine, L-Amphetamine, D,L-Amphetamine, Phentermine, Methylphenidate and Nicotine.

2. Analgesics and/or Anti-Migraine such as Acetaminophen, Acetylsalicylic Acid, Buprenorphine, Codeine, Fentanyl, Lisuride, Salicylic Acid derivatives and Sumatriptan.

3. Androgen agents such as Fluoxymesterone, Methyl Testosterone, Oxymesterone, Oxymetholone, Testosterone and Testosterone derivatives.

4. Anesthetic agents such as Benzocaine, Bupivicaine, Cocaine, Dibucaine, Dyclonine, Etidocaine, Lidocaine, Mepivacaine, Prilocaine, Procaine and Tetracaine.

5. Anoretic agents such as Fenfluramine, Mazindol and Phentermine.

6. Anti-Bacterial (antibiotic) agents including Aminoglycosides, β-Lactams, Cephamycins, Macrolides, Penicillins, Polypeptides and Tetracyclines.

7. Anti-Cancer agents such as Aminolevulinic Acid and Tamoxifen.

8. Anti-Cholinergic agents such as Atropine, Eucatropine and Scopolamine.

9. Anti-Diabetic agents such as Glipizide, Glyburide, Glypinamide and Insulins.

10. Anti-Fungal agents such as Clortrimazole, Ketoconazole, Miconazole, Nystatin and Triacetin.

11. Anti-Inflammatory and/or Corticoid agents such as Beclomethasone, Betamethasone, Betamethasone Dipropionate, Betamethasone Valerate, Corticosterone, Cortisone, Deoxycortocosterone and Deoxycortocosterone, Acetate, Diclofenac, Fenoprofen, Flucinolone, Fludrocortisone, Fluocinonide, Fluradrenolide, Flurbiprofen, Halcinonide, Hydrocortisone, Ibuprofen, Ibuproxam, Indoprofen, Ketoprofen, Ketorolac, Naproxen, Oxametacine, Oxyphenbutazone, Piroxicam, Prednisolone, Prednisone, Suprofen and Triamcinolone Acetonide.

12. Anti-Malarial agents such as Pyrimethamine.

13. Anti-Parkinson's and/or Anti-Alzhiemer's agents such as Bromocriptine, 1-Hydroxy-Tacrine, Levodopa, Lisaride Pergolide, Pramipexole, Ropinirole, Physostigimine, Tacrine Hydrochloride and Teruride.

14. Anti-Psychotic and/or Anti-Anxiety agents such as Acetophenazine, Azapirones, Bromperidol, Chlorproethazine, Chlorpromazine, Fluoxetine, Fluphenazine, Haloperidol, Loxapine, Mesoridazine, Molindone, Ondansetron, Perphenazine, Piperacetazine, Thiopropazate, Thioridazine, Thiothixene, Trifluoperazine and Triflupromazine.

15. Anti-Ulcerative agents such as Enprostil and Misoprostol.

16. Anti-Viral agents such as Acyclovir, Rimantadine and Vidarabine.

17. Anxiolytic agents such as Buspirone, Benzodiazepines such as Alprazolam, Chlordiazepoxide, Clonazepam, Clorazepate, Diazepam, Flurazepam, Halazepam, Lorazepam, Oxazepam, Oxazolam, Prazepam and Triazolam.

18. β-Adrenergic agonist agents such as Albuterol, Carbuterol, Fenoterol, Metaproterenol, Rimiterol, Quinterenol, Salmefamol, Soterenol, Tratoquinol, Terbutaline and Terbuterol.

19. Bronchodilators such as Ephedrine derivatives including Epiniphrine and Isoproterenol, and Theophylline.

20. Cardioactive agents such as Atenolol, Benzydroflumethiazide, Bendroflumethiazide, Calcitonin, Captopril, Chlorothiazide, Clonidine, Dobutamine, Dopamine, Diltiazem, Enalapril, Enalaprilat, Gallopamil, Indomethacin, Isosorbide Dinitrate and Mononitate, Nicardipine, Nifedipine, Nitroglycerin, Papaverine, Prazosin, Procainamide, Propranolol, Prostaglandin $E_1$, Quinidine Sulfate, Timolol, and Verapamil.

21. α-Adrenergic agonist agents such as Phenylpropanolamine.

22. Cholinergic agents such as Acetylcholine, Arecoline, Bethanechol, Carbachol, Choline, Methacoline, Muscarine and Pilocarpine.

23. Estrogens such as Conjugated Estrogenic Hormones, Equilenin, Equilin, Esterified Estrogens, Estradiol, 17β-Estradiol, Estradiol Benzoate, 17β-Estradiol Valerate, Estradiol 17β-Cypionate, Estriol, Estrone, Estropipate, 17β-Ethinyl Estradiol and Mestranol.

24. Muscle relaxants such as Baclofen.

25. Narcotic antagonist agents such Nalmfene and Naloxone.

26. Progestational agents such as Chlorrnadinone and Chlormadinone Acetate, Demegestone, Desogestrel, Dimethisterone, Dydrogesterone, Ethinylestrenol, Ethisterone, Ethynodiol and Ethynodiol Diacetate, Gestodene, 17α-Hydroxyprogesterone, Hydroxygesterone Caproate, Medroxyprogesterone and Medroxyprogesterone Acetate, Megestrol Acetate, Melengestrol, Norethindrone and Norethidrone Acetate, Norethynodrel, Norgesterone, Norgestrel, 19-Norprogesterone, Progesterone, Promegestone and esters thereof. Free base forms of drugs which have a greater affinity for the acid (carboxyl) functional group in a carboxyl functional acrylic-based polymer are preferred in some applications.

The drugs and mixtures thereof can be present in the composition in different forms, depending on which form yields the optimum delivery characteristics. Thus, in the case of drugs, the drug can be in its free base or acid form, or in the form of salts, esters, prodrugs, specific enantiomers or racemates, or any other pharmacologically acceptable derivatives, or as components of molecular complexes.

Preferred drugs include crystalline drugs, such as, for example, estradiol, norethindrone acetate, testosterone, scopolamine As used herein, "therapeutically effective" means an amount of an active agent that is sufficient to achieve the desired local or systemic effect or result, such as to prevent, cure, diagnose, mitigate or treat a disease or condition, when applied topically over the duration of intended use. The amounts necessary are known in the literature or may be determined by methods known in the art, but typically range from about 0.1 mg to about 20,000 mg, and preferably from about 0.1 mg to about 1,000 mg, and most preferably from about 0.1 to about 500 mg per human adult or mammal of about 75 kg body weight per 24 hours.

The amount of drug to be incorporated in the composition varies depending on the particular drug, the desired therapeutic effect, and the time span for which the device is to provide therapy. For most drugs, the passage of the drugs through the skin will be the rate-limiting step in delivery. Thus, the amount of drug and the rate of release is typically selected so as to provide transdermal delivery characterized by a zero order time dependency for a prolonged period of time. The minimum amount of drug in the system is selected based on the amount of drug which passes through the skin in the time span for which the device is to provide therapy. Normally, the amount of drug in the system can vary from about (11% to about 50%. However, the composition of this invention is particularly useful for drugs which are used in relatively low concentrations, especially 0.3% to 30% of the total composition, more preferably from about 0.5% to about 15% of the total composition, most preferably from about 1% to about 10% of the total composition.

As used herein, the term "supersaturated" used in reference to the drug means that the amount of drug present is in excess of its solubility or dispersability in a multiple polymer adhesive system.

As used herein "flux" is defined as the percutaneous absorption of drugs through the skin, and is described by Fick's first law of diffusion:

$$J=-D(dC_m/dx),$$

where J is the flux in $g/cm^2/sec$, D is the diffusion coefficient of the drug through the skin in $cm^2/sec$ and $dC_m/dx$ is the concentration gradient of the active agent across the skin or mucosa.

The invention resulted from the discovery that the transdermal permeation rate of a drug from the pressure-sensitive adhesive system can be selectively modulated by adjusting the monomeric make up of the acrylic based polymer in the system. As used herein, the term "transdermal permeation rate" means the rate of passage of the drug through the skin; which, as known in the art, may or may not be affected by the rate of release of the drug from the carrier.

Solubility parameter, also referred to herein as "SP," has been defined as the sum of all the intermolecular attractive forces, which are empirically related to the extent of mutual solubility of many chemical species. A general discussion of solubility parameters is found in an article by Vaughan, "Using Solubility Parameters in Cosmetics Formulation," *J. Soc. Cosmet. Chem.*, Vol. 36, pages 319-333 (1985).

The present invention relates to a drug-in-adhesive system that is preferably formulated so that it is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In general, the multiple polymer adhesive system should have a glass transition temperature (Tg), measured using a differential scanning calorimeter, of between about −70° C. and 70° C.

The drug-in-adhesive system preferably includes at least one acrylic-based polymer, one polysiloxane or rubber and an active agent, where the monomeric make-up of the acrylic-based polymer modulates the drug delivery characteristics. In addition to selecting the monomeric makeup of the acrylic-based polymer, forming a blend of multiple polymers results in an adhesive system having a characteristic "net solubility parameter," the selection of which advantageously permits a selectable modulation of the delivery rate of the drug by adjusting the solubility of the drug in the multiple polymer adhesive system.

The term "acrylic-based" polymer is defined as any polyacrylate, polyacrylic, acrylate and acrylic polymer. The acrylic-based polymers can be any of the copolymers, terpolymers, and the like of various acrylic acids or esters. The acrylic-based polymers useful in practicing the invention are polymers of one or more monomers of acrylic acids and other copolymerizable monomers. The acrylic-based polymers also can include copolymers of alkyl acrylates and/or methacrylates and/or copolymerizable secondary monomers. The acrylic-based polymer may be functional or non functional.

As used herein, "functionality" is broadly defined as a measure of the type and quantity of functional groups that a particular acrylic-based polymer has.

As used herein, "functional monomers or groups," are monomer units in acrylic-based polymers which have reactive chemical groups which modify the acrylic-based polymers directly or provide sites for further reactions. Examples of functional groups include carboxyl, epoxy and hydroxy groups.

As used herein "non-functional acrylic-based polymer" is defined as an acrylic-based polymer that has no or substantially no functional reactive moieties present in the acrylic. These are generally acrylic esters which can be copolymerized with other monomers which do not have functional groups, such as vinyl acetate.

The term "carrier" as used herein refers to any non-aqueous material known in the art as suitable for transdermal drug delivery administration, and includes any polymeric material into which an active agent may be solubilized in combination or admixture with the other ingredients of the composition. The polymeric materials preferably comprise adhesives and, in particular, pressure-sensitive adhesives. The carrier material is typically used in an amount of about 40% to about 95%, and preferably from about 50% to about 80%, by weight based on the dry weight of the total carrier composition.

The term carrier composition may also refer to enhancers, solvents, co-solvents and other types of addictives useful for facilitating transdermal drug delivery.

The acrylic-based polymer according to the present invention is preferably polymerized from at least two monomers. The first monomer includes at least one soft acrylic monomer and the second monomer includes at least one hard acrylic monomer.

As used herein, the term "soft acrylic monomer" is intended to refer to a monomer which is present in the transdermal drug delivery system as one monomer in the acrylic pressure-sensitive adhesive that has a glass transition temperature ($T_g$) from about −70° C. to about −10° C., more preferably from about −60° C. to about −20° C., and most preferably from about −60° C. to about −24° C. Some examples of soft acrylic monomers include: 2-ethyl hexyl acrylate, isobutyl acrylate, ethyl acrylate, butyl acrylate, dodecyl methacrylate, 2-ethylhexyl methacrylate, 2-ethoxyethyl acrylate, isopropyl acrylate, and 2-methoxyethyl acrylate.

As used herein, the term "hard acrylic monomer" is intended to refer to a monomer which is present in the transdermal drug delivery system as a one monomer in the acrylic pressure sensitive adhesive that has a glass transition temperature ($T_g$) from about −5° C. to about 120° C., more preferably from about 10° C. to about 120° C., and most preferably from about 10° C. to about 105° C. Some examples of hard acrylic monomers include: methacrylate, N-butyl acrylate, acrylic acid, butyl methacrylate, ethyl methacrylate, methyl methacrylate, hexyl methacrylate, and methyl acrylate.

Values for the glass transition temperatures are based upon literature values most commonly reported for the homopolymers of the corresponding monomers.

The amount of soft acrylic monomer that makes up the acrylic based polymer according to the present invention ranges from about 20 to about 70% by weight of the acrylic based polymer. The amount of hard acrylic monomer that makes up the acrylic based polymer according to the present invention ranges from about 30 to about 80% by weight of the acrylic based polymer. The ratio of hard monomers to soft monomer in the acrylic based polymer according to the present invention is dependent on the specific active agent to be delivered from the transdermal device as well as the desired drug permeation, delivery rates and profiles to be selectively modulated.

In the practice of the preferred embodiments of the invention, the acrylic-based polymer constitutes from about 2% to about 95% of the total dry weight of the of the carrier composition, and preferably from about 2% to about 90%, and more preferably from about 2% to about 85%, wherein the amount of the acrylic-based polymer is dependent on the amount and type of drug used.

The acrylic-based polymers usable in the invention are polymers of one or more monomers of acrylic acids and other copolymerizable monomers. The acrylate polymers also include copolymers of alkyl acrylates and/or methacrylates and/or copolymerizable secondary monomers or monomers with functional groups. By varying the amount of each type of monomer added, the cohesive properties of the resulting acrylate polymer can be changed as is known in the art. In general, the acrylate polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, methacrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

Suitable acrylic-based polymers may also be a pressure-sensitive adhesive which are commercially available and include the acrylic-based adhesives sold under the trademarks Duro-Tak® by National Starch and Chemical Corporation, Bridgewater, N.J. (such as 87-2287, -4098, -2852, -2196, -2296, -2194, -2516, -2070, -2353, -2154, -2510, -9085, -9088 and 73-9301). Other suitable acrylic-based adhesives include those sold under the the trademark EUDRAGIT® by Roehm Pharma GmbH, Darmstadt, Germany; those sold by Cytec Surface Specialties; St. Louis, Mo., under the trademarks Gelva® Multipolymer Solution (such as 2480, 788, 737, 263, 1430, 1753, 1151, 2450, 2495, 3067, 3071, 3087 and 3235).

Combinations of acrylic-based polymers based on their functional groups is also contemplated. Acrylic-based polymers having functional groups are copolymers or terpolymers which contain in addition to nonfunctional monomer units, further monomer units having free functional groups. The monomers can be monofunctional or polyfunctional. These functional groups include carboxyl groups, hydroxy groups, amino groups, amido groups, epoxy groups, etc. Preferred functional groups are carboxyl groups and hydroxy groups. Preferred carboxyl functional monomers include acrylic acid, methacrylic acid, itaconic acid, maleic add, and crotonic acid. Preferred hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxy hexyl acrylate, hydroxyhexyl methacrylate. Non-functional acrylic-based polymers can include any acrylic based polymer having no or substantially no free functional groups. The acrylic based polymer can include copolymers, terpolymers and multipolymers. The monomers used to produce the polymers can include alkyl acrylic or methacrylic esters such as methyl acrylate, ethyl acrylate, propyl acrylate, amyl acrylate, butyl acrylate, 2-ethylbutyl acrylate, hexyl acrylate, heptyl acrylate, octyl acrylate, nonyl acrylate, 2-ethylhexyl acrylate, decyl acrylate, dodecyl acrylate, tridecyl acrylate, glycidyl acrylate and the corresponding methacrylic esters.

Both the acrylic-based polymer having substantially no functional groups and acrylic-based polymers having functional groups can optionally include further modifying monomers. These modifying monomers can include any conceivable monomer that is capable of undergoing vinyl polymerization. For example, the incorporation of styrene monomers can be used to increase the glass transition temperature and are sometimes used to improve the cohesive strength. The copolymerization of vinyl acetate monomers with acrylic esters are also used to form acrylic-based polymers. Ethylene can also be copolymerized with acrylic esters and vinyl acetate to give suitable acrylic-based polymers.

For example, a composition will require less of a functional acrylic that contains 20% by weight of functional groups as opposed to one that contains 0.5% by weight of functional groups to achieve the same effect required for solubility and flux. Broadly speaking, the amount of functional acrylic is generally within the range of about 1 to 99 weight % and preferably 5 to 95 weight %, more preferably 20 to 75 weight %, even more preferably 30 to 65 weight %, based on the total polymer content of the transdermal composition. The amount of non-functional acrylic or acrylic with a functional group which does not have as great of an affinity for the drug, is within the range of about 99 to 1 weight %, preferably 95 to 5 weight %, more preferably 75 to 20 weight % and even more preferably 30 to 65 weight % based on the total polymer content of the composition.

Further details and examples of acrylic-based adhesives, functional monomers, and polymers which have no functional groups and which are suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, N.Y. (1989); "Acrylic and Methacrylic Ester Polymers," Polymer Science and Engineering, Vol. 1, 2nd ed., pp 234-268, John Wiley & Sons, (1984); U.S. Pat. No. 4,390,520; and U.S. Pat. No. 4,994,267 all of which are expressly incorporated by reference in their entireties.

The required proportions of acrylic-based or other polymers used are generally dependant on the specific drug, its desired delivery rate and the desired duration of drug delivery. In general, proportions of acrylic-based polymers also depend on the content of the functional monomer units in the functional acrylic.

As used herein, the term "rubber" refers to a viscoelastic material which has the properties of a pressure-sensitive adhesive and which contains at least one natural or synthetic elastomeric polymer. Suitable rubbers include silicone based polymers such as polysiloxane, polyisobutylene and natural rubber, with polysiloxane being preferred.

The term "silicone-based" polymer is intended to be used interchangeably with the terms siloxane, polysiloxane, and silicones as used herein and as known in the art. The silicone-based polymer may also be a pressure-sensitive adhesive, with a polysiloxane adhesive prepared by cross-linking an elastomer, typically a high molecular weight polydiorganosiloxane, with a resin, to produce a three-dimensional siloxane structure, via a condensation reaction in an appropriate organic solvent. The ratio of resin to elastomer is a critical factor that can be adjusted in order to modify the physical properties of polysiloxane adhesives. Sobieski, et al., "Silicone Pressure Sensitive Adhesives," Handbook of Pressure-Sensitive Adhesive Technology. 2nd ed., pp. 508-517 (D. Satas, ed.), Van Nostrand Reinhold., New York (1989). Further details and examples of silicone pressure-sensitive adhesives which are useful in the practice of this invention are described in the following U.S. Pat. Nos. 4,591,622; 4,584,355; 4,585,836; and 4,655,767, all expressly incorporated by reference in their entireties. Suitable silicone pressure-sensitive adhesives are commercially available and include the silicone adhesives sold under the trademarks BIO-PSA® by Dow Corning Corporation, Medical Products, Midland, Mich. such as -4100 series, -4200 series, -4300 series, -4400 series, -4500, and -4600 series. Capped silicones with high resin content are preferred. It should be also understood that silicone fluids are also contemplated as being used in the present invention.

Other rubber-based pressure-sensitive adhesives useful in practicing the invention include hydrocarbon polymers such as natural and synthetic polyisoprene; polybutylene; polyisobutylene; styrene based polymers; styrene block copolymers; butadiene based polymers; styrene/butadiene polymers; styrene-isoprene-styrene block copolymers; hydrocarbon polymers such as, for example, butyl rubber; halogen-containing polymers such as, for example, poly-acrylo-nitrile, polytetrafluoroethylene, polyvinylchloride, polyvinylidene chloride, and polychlorodiene; and other copolymers thereof.

Further details and examples of silicone pressure-sensitive adhesives which are useful in the practice of this invention are described in the following U.S. Pat. Nos. 4,591,622; 4,584,355; 4,585,836; and 4,655,767. These patents are incorporated herein by reference.

The carrier composition may comprise blends of acrylic-based polymers, silicone-based polymers or silicone fluids and rubbers based upon their differing solubility parameters, alone or in combination with other polymers, for example polyvinylpyrrolidone, as more fully described in U.S. Pat. Nos. 5,474,783; 5,656,286; 5,958,446; 6,024,976; 6,221,383; and 6,235,306; which are incorporated herein in their entirety. The amount of each polymer is selected to adjust the saturation concentration of the drug in the multiple polymer system, and to result in the desired rate of delivery of the drug from the system and through the skin or mucosa.

In the practice of preferred embodiments of the invention, the rubber-based pressure sensitive adhesive constitutes from about 9% to about 97% of the total weight of the pressure-sensitive adhesive composition, preferably about 12% to about 97%, and more preferably from about 14% to about 94%, and most preferably from about 18 to 90% of the total weight of the pressure-sensitive adhesive composition.

The weight per unit area of the dried contact adhesive layer (matrix) is usually in the range of from about 1 $mg/cm^2$ to about 20 $mg/cm^2$, and more preferably in the range of from about 2.5 $mg/cm^2$ to about 15 $mg/cm^2$. The delivery rate is in the range of from about 0.01 mg to about 100 mg of active agent per day, and more preferably in the range of from about 0.1 mg to about 50 mg per day.

Generally, the amount of drug sufficient to deliver a therapeutically effective amount of the active agent at a substantially zero-order kinetic rate of delivery for an extended period of time of at least three days and up to seven days or longer, and to eliminate or suppress the high initial release rate of a drug subject to a first order release profile.

Those skilled in the art can readily determine the rate of delivery of drugs from the carrier composition in order to select suitable combinations of polymers and drug for a particular application. Various techniques can be used to determine the rate of delivery of the drug from the polymer. Illustratively, the rate of delivery can be determined by measuring the transfer of drug from one chamber to another through cadaver skin over time, and calculating, from the obtained data, the drug delivery or flux rate.

Of course, the composition of the transdermal drug delivery system can also contain agents known to accelerate the delivery of the drug through the skin. These agents have been referred to as skin penetration enhancers, accelerants, adjuvants, and sorption promoters, and are collectively referred to herein as "enhancers." This class of agents includes those with diverse mechanisms of action including those which have the function of improving the solubility and diffusibility of the drug within the multiple polymer and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the delivery of the drug. An enhancer may be included in a drug delivery system up then the enhancer is preferably present in an amount of about 1% to about 10% by weight. Some examples of enhancers are polyhydric alcohols such as dipropylene glycol, propylene glycol, and polyethylene glycol which enhance drug solubility; oils such as olive oil, squalene, and lanolin; polyethylene glycol ethers and fatty ethers such as cetyl ether and oleyl ether; fatty acid esters such as isopropyl myristate which enhance drug diffusibility; fatty acid alcohols such as oleyl alcohol; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surf actants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, isopropyl palmitate, oleamide, polyoxyethylene (4) lauryl ether, polyoxyethylene (2) oleyl ether and polyoxyethylene (10) oleyl ether sold under the trademarks Brij 30, 93 and 97 by ICI Americas, Inc., and polysorbate 20 sold under the trademark Tween 20 by Id Americas, Inc.

In certain embodiments of the invention a plasticizer or tackifying agent is incorporated into the formulation to improve the adhesive characteristics of the pressure-sensitive adhesive composition. A tackifying agent is particularly useful in those embodiments in which the drug does not plasticize the polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood resins or rosins. The tackifying agent employed is preferably compatible with the blend of polymers. In preferred embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where a synthetic rubber, for example, is a major component, mineral oil is a preferred tackifying agent. Acrylics can be tackified with oleates, oleic acid, oleyl alcohol and other fatty acid-derived agents.

Some drugs function as plasticizers in the composition because they are soluble to a certain degree in the polymers comprising the system. For drug molecules which are not readily soluble in the polymer system, a co-solvent for the drug and polymer can be added. Co-solvents, such as lecithin, retinol derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the drug in the multiple polymer adhesive system.

To summarize, the preferred and optimum compositions are as follows:

TABLE I

| | PERCENT BY WEIGHT | |
| --- | --- | --- |
| Component | Preferred Range | Optimum Range |
| Acrylic based polymer | 2-95 | 2-85 |
| Polysiloxane | 97-4 | 97-14 |
| Co-solvent(s) | 0-30 | 0-20 |
| Enhancer(s) | 0-20 | 0-15 |
| Total Drug(s) | 0.1-50 | 0.3-30 |

The compositions of this invent-ion may further be provided with various thickeners, fillers and other additives known for use with transdermal drug delivery systems. Where the composition tends to absorb water, for example, when lecithin is used as a co-solvent, hydrophilic substances are especially useful. One type of hydrophilic substance which has been successfully employed is clay. The addition of clay has been found to improve adhesiveness in transdermal formulations without reducing the rate of drug delivery. Suitable clays include kaolinites such as baolinite, anauxite, dickite and nacrite, montrnorillonites such as montinorillonite, bentonite, berdellite and montronite, illites/muscovites such as illite and glauconite, chlorites, polygorshites such as attapulgite, halloysite, metabolloysite, allopharte and aluminum silicate clays.

In a device aspect of the invention, the pressure-sensitive adhesive composition can be used as an adhesive portion of any transdermal drug delivery system (e.g., a reservoir device) or it can comprise an adhesive monolithic. Of course, the principles of the invention would still apply to embodiments where the transdermal drug delivery composition is not a pressure-sensitive adhesive and comprises a drug reservoir.

A device, or individual dosage unit, of the present invention can be produced in any manner known to those of skill in the art. After the dermal composition is formed, it may be brought into contact with an occlusive backing layer in any manner known to those of skill in the art. Such techniques include calendar coating, hot melt coating, solution coating, etc. Of course, occlusive backing materials are well known in the art and can comprise plastic films of polyethylene, vinyl acetate resins, polyester, polypropylene, BAREX®, ethylene/vinyl acetate copolymers, polyvinyl chloride, polyurethane, and the like, metal foils, non-woven fabric, cloth, coextrusion or laminations of the above and commercially available laminates. The occlusive backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Release International designated Bio-Release® liner and Syl-off® 7610 liner. For preferred embodiments in which a polysiloxane is part of the multiple polymer adhesive system, the release liner must be compatible with the silicone adhesive. An example of a suitable commercially available liner is 3M's 1022 Scotch Pak.

The configuration of the transdermal delivery system of the present invention can be in any shape or size as is necessary or desirable. Illustratively, a single dosage unit may have a surface area in the range of 1 to 200 $cm^2$. Preferred sizes are from 5 to 60 $cm^2$.

In a method aspect of the invention, a plurality of polymers are blended (but not chemically reacted or cross-linked) to result in a pressure-sensitive adhesive composition which controls delivery of an incorporated drug through the skin or mucosa. The term "blending," of course, incorporates choosing the appropriate polymeric components, and the proportions thereof, to achieve the desired effect.

Drug is blended with the pressure sensitive adhesives to solublize the drug into the pressure sensitive adhesive composition. Customary substances such as fillers, skin-protective substances, tackifiers or the like may be added if desired, but it is not essential. The mixture is then blended together to form a flexible finite composition. The system is freed of solvent in a dryer located downstream. After leaving the dryer, the then dry and self-adhesive active ingredient/adhesive matrix is laminated with a further layer, which may be e.g. a plastics film, a non-woven fabric, a plastics foam, a woven fabric or the like, for covering purposes.

An exemplary general method for the preparation of a preferred embodiment is as follows:

1. Appropriate amounts of acrylic based polymer, polysiloxane pressure sensitive adhesive, solvent(s), enhancer(s), and organic solvent(s) (for example toluene) are combined and thoroughly mixed together in a vessel.

2. The drug is then added to the mixture and agitation is carried out until the drug is uniformly mixed in.

3. The formulation is then transferred to a coating operation where it is coated onto a protective release liner at a controlled specified thickness. The coated product is then passed through an oven in order to drive off all volatile processing solvents.

4. The dried product on the release liner is then joined to the backing material and wound into rolls for storage.

5. Appropriate size and shape "systems" are die-cut from the roll material and then pouched.

The order of steps, the amount of the ingredients, and the amount and time of agitation or mixing may be importance process variables which will depend on the specific polymers, drug, cosolvents, and enhancers used in the formulation. These factors can be adjusted by those skilled in the art, while keeping in mind the object of providing a uniform product. It is believed that a number of other methods, including changing some of the order of steps, can be carried out and will give desirable results. In addition to having various shapes, the dosage units produces may come in various sizes. A surface area in the range of 1 to 200 square centimeters is contemplated, and the presently preferred sizes are: 5, 10, 15, 20, 30, 30 and 60 are centimeters.

The present invention is illustrated by the following examples, without limiting the scope of the invention.

EXAMPLES

The following specific examples are included as illustrative of dermal compositions, and methods of making same, within the contemplation of the invention. These examples are in no way intended to be limiting of the scope of the invention.

A polymer mixture was prepared by combining the following ingredients. The amount of the ingredients set forth in these examples are on a percentage "dry" basis of the carrier composition, that is, after removal of volatile process solvents.

Examples 1-3

|  | Example 1 | Example 2 | Example 3 |
|---|---|---|---|
| Acrylic-based polymer (70% soft monomers/30% hard monomers) | 20 | | |
| Acrylic-based polymer (50% soft monomers/50% hard monomers) | | 20 | |
| Acrylic-based polymer (20% soft monomers/80% hard monomers) | | | 20 |
| Silicone-based polymer (BIO-PSA 4503) | 62 | 62 | 62 |
| Oleyl Alcohol | 6 | 6 | 6 |
| PVP (Kollidon 30) | 10 | 10 | 10 |
| 17 β Estradiol | 2 | 2 | 2 |

The average flux profiles of Examples 1-3 are illustrated in FIG. 1.

Examples 4-6

|  | Example 4 | Example 5 | Example 6 |
|---|---|---|---|
| Acrylic-based polymer (70% soft monomers/30% hard monomers) | 20 | | |
| Acrylic-based polymer (50% soft monomers/50% hard monomers) | | 20 | |
| Acrylic-based polymer (20% soft monomers/80% hard monomers) | | | 20 |
| Silicone-based polymer (BIO-PSA 4503) | 62 | 62 | 62 |
| Oleyl Alcohol | 6 | 6 | 6 |
| PVP (Kollidon 30) | 10 | 10 | 10 |
| Norethindrone Acetate | 2 | 2 | 2 |

Figure 2:
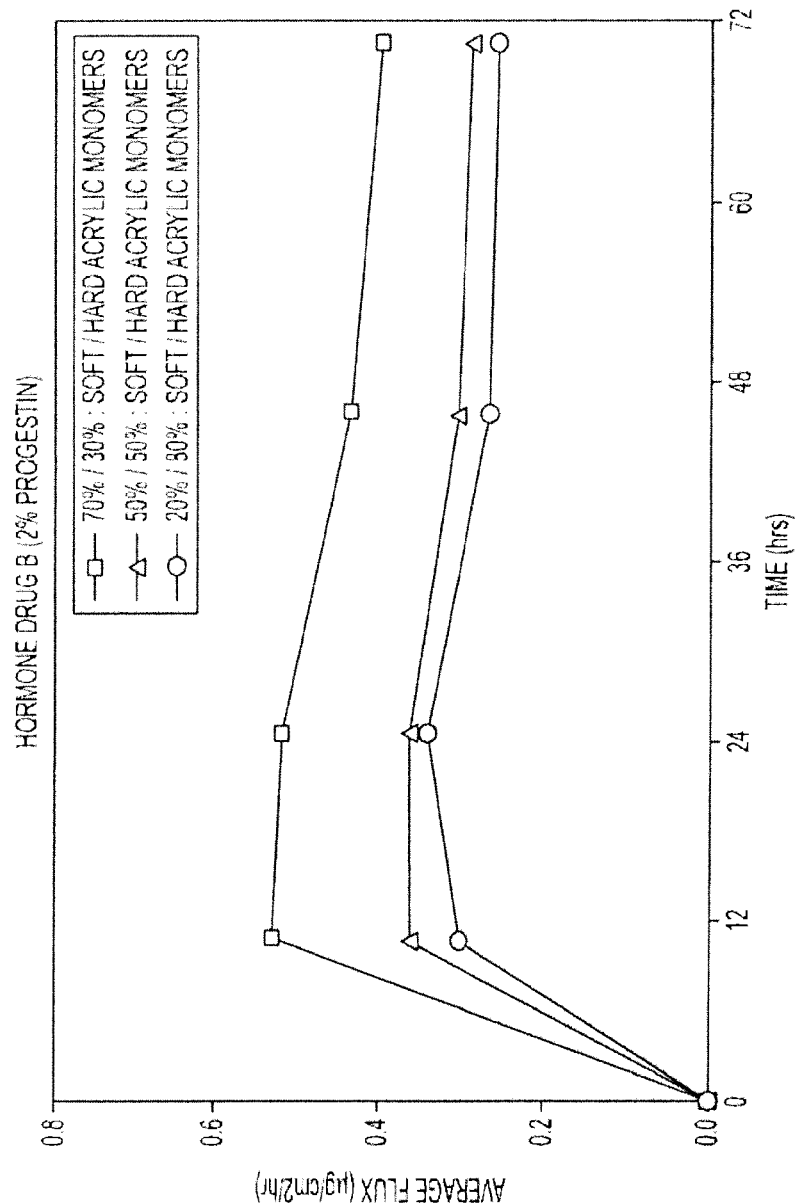
FIG. 2 is a graphic representation of the effects on drug delivery, onset and profile of norethindrone acetate with different proportions of hard and soft acrylic-based monomers in the pressure sensitive adhesives.

The average flux profiles of Examples 4-6 are illustrated in FIG. 2.

Examples 7-8

|  | Example 7 | Example 8 |
|---|---|---|
| Acrylic-based polymer (50% soft monomers/50% hard monomers) | 40 | |
| Acrylic-based polymer (20% soft monomers/80% hard monomers) | | 40 |
| Silicone-based polymer (BIO-PSA 4503) | 40 | 40 |
| Oleyl Alcohol | 6 | 6 |
| Dipropylene glycol | 8 | 8 |
| PVP (Kollidon 30) | 10 | 10 |
| Testosterone | 2 | 2 |

Figure 3:
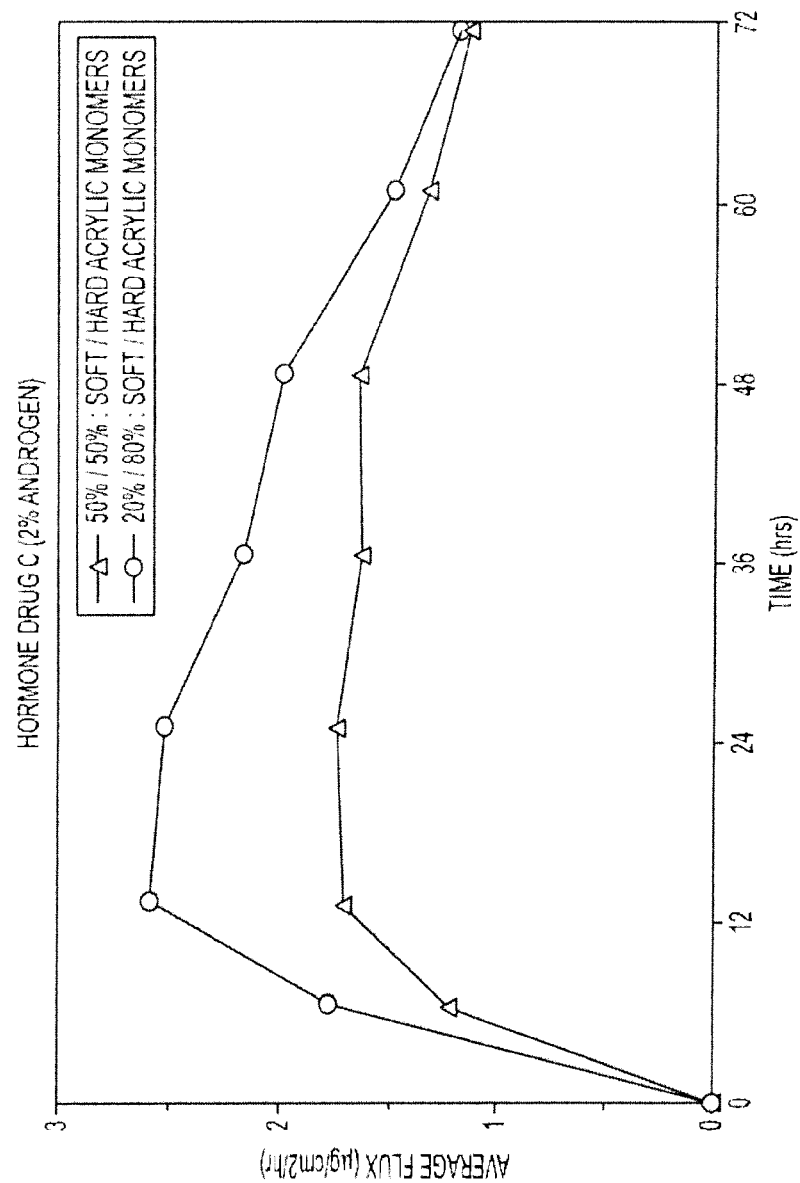
FIG. 3 is a graphic representation of the effects on drug delivery, onset and profile of testosterone with different proportions of hard and soft acrylic-based monomers in the pressure sensitive adhesives.

The average flux profiles of Examples 7-8 are illustrated in FIG. 3.

Examples 9-11

|  | Example 9 | Example 10 | Example 11 |
|---|---|---|---|
| Acrylic-based polymer (70% soft monomers/30% hard monomers) | 73 | | |
| Acrylic-based polymer (50% soft monomers/50% hard monomers) | | 73 | |
| Acrylic-based polymer (20% soft monomers/80% hard monomers) | | | 73 |

-continued

|  | Example 9 | Example 10 | Example 11 |
|---|---|---|---|
| Silicone-based polymer (BIO-PSA 4503) | 12 | 12 | 12 |
| Oleyl Alcohol | 6 | 6 | 6 |
| Dipropylene glycol | 3 | 3 | 3 |
| Scopolamine | 2 | 2 | 2 |

Figure 4:
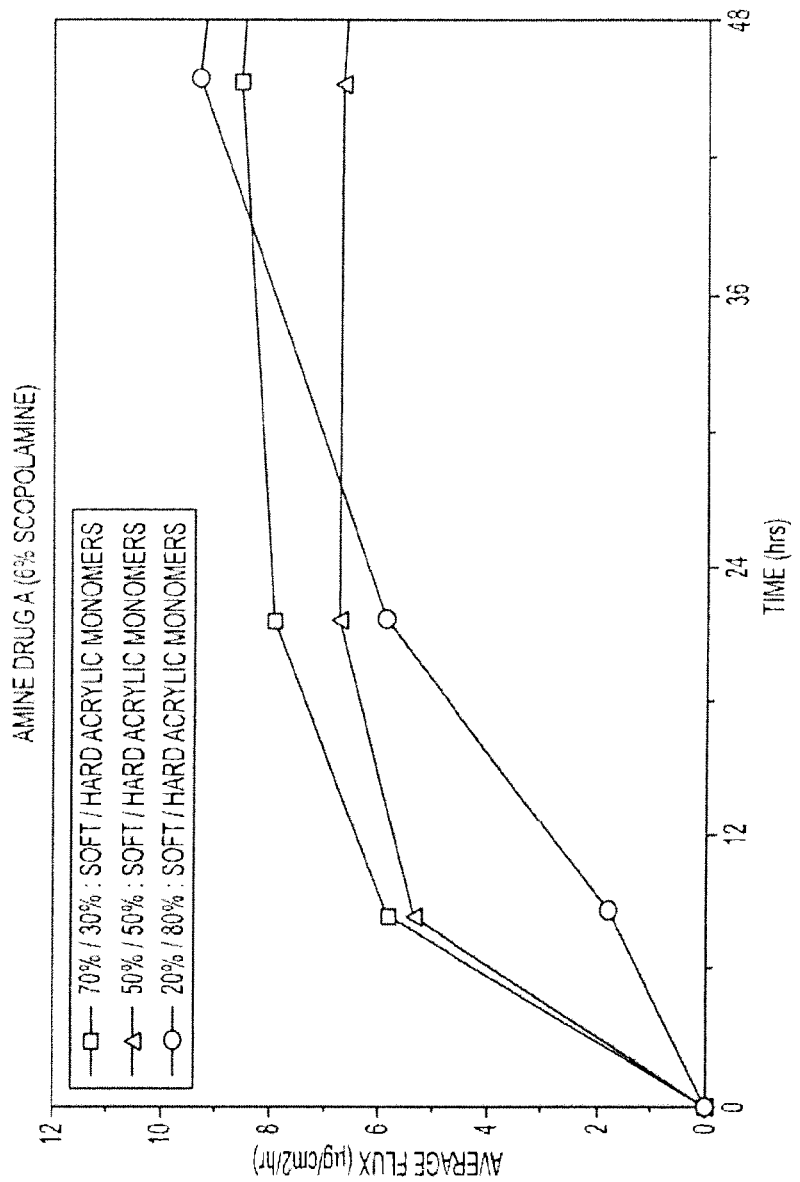
FIG. 4 is a graphic representation of the effects on drug delivery, onset and profile of scopolamine with different proportions of hard and soft acrylic-based monomers in the pressure sensitive adhesives.

The average flux profiles of Examples 9-11 are illustrated in FIG. 4.

As can be seen from the Figures, the in-vitro permeation rate for each transdermal drug matrix varied depending upon which acrylic polymer was utilized in the matrix. These results indicate that drug delivery rate and profile can be manipulated by modifying the acrylic monomer composition of the acrylic pressure sensitive adhesive in the transdermal drug delivery device.

The above description and example are only illustrative of preferred embodiments which achieve the objects, features, and advantages of the present invention, and it is not intended that the present invention be limited thereto.

What is claimed is:

1. A method for transdermally delivering a drug to a user in need thereof, comprising administering to the user a transdermal drug delivery system comprising a polymer composition comprising a blend of:
   (a) at least one acrylic-based polymer which acrylic-based polymer is polymerized with monomers that include:
      (i) a soft acrylic monomer having a glass transition temperature ($T_g$) from about −70° C. to about −10° C. in an amount of from about 20 to about 70% by weight of the acrylic-based polymer; and (ii) a hard acrylic monomer having a glass transition temperature ($T_g$) from about −5° C. to about 120° C. in an amount of from about 30 to about 80% by weight of the acrylic-based polymer; and
   (b) about 0.3% to about 30% by weight of the composition of one or more drugs,
   wherein said acrylic based polymers are not polymerized with methacrylic acid monomers.

2. The method according to claim 1, wherein the one or more drugs comprises methylphenidate.

3. The method according to claim 1, wherein the composition comprises from about 0.5% to about 15% by weight of the one or more drugs.

4. The method according to claim 1, wherein the composition comprises from about 1% to about 10% by weight of the one or more drugs.

5. The method according to claim 1, wherein the composition comprises from 0.3% to 30% by weight of the one or more drugs.

6. The method according to claim 1, wherein the soft acrylic monomer has a glass transition temperature ($T_g$) from about −60° C. to about −20° C.

7. The method according to claim 1, wherein the soft acrylic monomer has a glass transition temperature ($T_g$) from about −60° C. to about −24° C.

8. The method according to claim 1, wherein the soft acrylic monomer is one or more selected from the group consisting of 2-ethyl hexyl acrylate, isobutyl acrylate, ethyl acrylate, butyl acrylate, dodecyl methacrylate, 2-ethylhexyl methacrylate, 2-ethoxyethyl acrylate, isopropyl acrylate, and 2-methoxyethyl acrylate.

9. The method according to claim 1, wherein the hard acrylic monomer has a glass transition temperature ($T_g$) from about 10° C. to about 120° C.

10. The method according to claim 1, wherein the hard acrylic monomer has a glass transition temperature ($T_g$) from about 10° C. to about 105° C.

11. The method according to claim 1, wherein the hard acrylic monomer is one or more selected from the group consisting of methacrylate, N-butyl acrylate, acrylic acid, butyl methacrylate, ethyl methacrylate, methyl methacrylate, hexyl methacrylate, and methyl acrylate.

12. The method according to claim 1, wherein the composition further includes a rubber-based polymer.

13. The method according to claim 12, wherein the acrylic-based polymer comprises from 2 to about 95% by weight of the composition and the rubber-based polymer comprises from 4 to about 97% by weight of the composition.

14. The method according to claim 12, wherein the rubber-based polymer is one or more selected from the group consisting of natural and synthetic polyisoprene, polybutylene, polyisobutylene, styrene based polymers, styrene block copolymers, butadiene based polymers, styrene/butadiene polymers, styrene-isoprene-styrene block copolymers, hydrocarbon polymers, and halogen-containing polymers.

15. The method according to claim 12, wherein the wherein the rubber-based polymer includes polyisobutylene.

16. The method according to claim 1, wherein the composition further includes a silicon-based polymer.

17. The method according to claim 16, wherein the acrylic-based polymer comprises from 2 to about 95% by weight of the composition and the silicon-based polymer comprises from 4 to about 97% by weight of the composition.

18. The method according to claim 16, wherein the silicon-based polymer includes a polysiloxane polymer.

* * * * *